United States Patent
Collazo

(10) Patent No.: US 9,005,300 B2
(45) Date of Patent: Apr. 14, 2015

(54) TIBIAL INSERT LOCKING MECHANISM

(75) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 93 days.

(21) Appl. No.: 13/597,414

(22) Filed: Aug. 29, 2012

(65) Prior Publication Data

US 2014/0067076 A1     Mar. 6, 2014

(51) Int. Cl.
*A61F 2/38* (2006.01)
*A61F 2/30* (2006.01)

(52) U.S. Cl.
CPC ....... *A61F 2/389* (2013.01); *A61F 2002/30616* (2013.01)

(58) Field of Classification Search
CPC .................................. A61F 2/38; A61F 2/389
USPC ....................... 623/20.14, 20.15, 20.32–20.34
See application file for complete search history.

(56) References Cited

U.S. PATENT DOCUMENTS

| | | | |
|---|---|---|---|
| 4,795,468 A | 1/1989 | Hodorek et al. | |
| 4,944,757 A | 7/1990 | Martinez et al. | |
| 5,108,442 A | 4/1992 | Smith | |
| 5,645,604 A | 7/1997 | Schneider et al. | |
| 6,004,352 A | 12/1999 | Buni | |
| 6,126,692 A | 10/2000 | Robie et al. | |
| 8,012,215 B2 | 9/2011 | Metzger et al. | |
| 8,617,250 B2 * | 12/2013 | Metzger | 623/20.32 |

* cited by examiner

*Primary Examiner* — Yashita Sharma
(74) *Attorney, Agent, or Firm* — Lerner, David, Littenberg, Krumholz & Mentlik, LLP

(57) ABSTRACT

A tibial implant includes a baseplate having a proximally facing surface surrounded at least in part by a proximally extending wall. The wall has a ramp surface extending from the wall towards the baseplate proximally facing baseplate surface and a bore located distally of the ramp. A polyethylene bearing insert is mounted on the baseplate and has a distally facing surface engaging the proximally facing surface of the baseplate. The distally facing bearing insert surface has a recess and the insert has a side surface with a passageway extending from the recess through the insert side surface. A spring detent is mounted in the bearing insert recess and has a moveable pin biased outwardly of the bearing insert side surface and into the bore of the baseplate.

21 Claims, 8 Drawing Sheets

TIBIAL INSERT LOCKING MECHANISM

BACKGROUND OF THE INVENTION

Artificial joints of the human body, including in particular knee and hip joints, have been available for 50 years or more and have been the subject of intense development for at least the last 20 years. The earliest designs provided metal-to-bone or metal-to-metal contact between the articulating surfaces of a joint. Friction and wear were significantly reduced in subsequent designs by the introduction of ultra-high molecular weight polyethylene (UHMWPE) as a load-bearing surface. For example, a typical knee joint prosthesis has a metal tibial component or baseplate with a polyethylene load-bearing surface in contact with a metal femoral component. Early designs of this type had polyethylene cemented to the tibia, but it is conventional today to secure a polyethylene bearing to a metal base or tray which is anchored in the tibia, typically with the aid of a stem or peg extending into the medullary canal of the tibia.

There are two general types of tibial components: modular and nonmodular. A nonmodular prostheses has a bearing secured to the base during fabrication in the factory, typically by direct compression molding. A modular prosthesis has a prefabricated bearing designed to be attached to the base during surgery.

A modular prosthesis has several advantages over non-modular prostheses, one of which is that an assortment of different prostheses, i.e., different base/bearing combinations, can be created in the operating room from a small inventory of separate bases and bearing of various sizes, shapes and other characteristics. With a modular prosthesis, an orthopedic surgeon can implant an appropriate base, such as a metal tray or baseplate, for the patient and then fit the patient with several trial bearings in the process of selecting an appropriate primary bearing to attach to the implanted base. Modular bearings are often readily removable, and in such cases they have the further advantage of facilitating revision surgery, which may become necessary in cases of traumatic injury or bearing surface wear, by enabling replacement of the bearing without removing the base.

BRIEF SUMMARY OF THE INVENTION

This invention relates to a locking mechanism for securing a modular tibial insert to a tibial baseplate to prevent disassociation of the assembly after implantation. The locking mechanism may also be used on tibial trial bearing components. It comprises a locking pin, a spring, a tibial insert, a recessed pocket for housing the spring, and a hole for housing the locking pin. The locking pin and spring are factory assembled to the insert to form a permanent assembly. An undercut groove at the bottom of the spring recessed pocket engages with one end of the spring to prevent dislodging during shipping and use.

After assembly, one end of the pin, which is under spring force, extends beyond the anterior surface of the insert. During assembly, a lead-in ramp on the anterior surface wall of the baseplate compresses the pin. After final seating of the insert on the baseplate, the compressed pin, under the spring tension forcibly extends and engages into a mating hole on the baseplate.

This locking mechanism allows for the easy removal of the insert from the baseplate without incurring damage to the insert and/or locking mechanism during the removal process. Easy and fast removal of the insert is advantageous in revision cases. In all surgical cases the ability to remove the insert not only easily and quickly but also without damage is especially important in cases where the surgeon may want to remove and reuse the insert after assembly should additional surgical work be required, such as recutting the tibia or femur. While this last scenario may not occur often, reusing the insert provides a cost benefit over opening up a new insert package.

To remove the insert, a handheld "pick" or probe is inserted through the hole on the baseplate from the anterior to compress the pin. With the pin compressed, the insert is carefully pried out of the baseplate. Many inserts in the marketplace employ one-way type locking mechanisms for example a snap mechanism using mechanical interlocks such as barbs or dovetails which are not only harder to remove but are often severely damaged during removal.

The invention relates to a tibial implant having a base plate with a distally facing bone contacting surface and a proximally facing surface surrounded, at least in part, by a proximally extending anterior wall. The wall has a ramped surface extending from the wall inwardly toward the base plate proximally facing surface. A receptacle, such as a groove, is located distally of the ramp.

A bearing insert is mounted on the base plate and has a distally facing surface engaging the proximally facing surface of the base plate. The distally bearing insert surface has a recess open to the insert distally facing surface. The insert has side surfaces extending proximally away from the baseplate proximally facing surface and has a passageway, such as a bore, extending from the recess in the insert to the insert side surface.

A spring detent includes a locking pin mounted in the bore of the insert and has a curved wire spring element mounted in the bearing insert recess. The wire spring element has an end engaging the pin for biasing the pin outwardly of the bearing insert anterior side surface. While the pin is described mounted in an anterior side of the bearing insert it may be located in any position where it is accessible during surgery.

The recess in the bearing insert may be a U-shaped slot extending proximally from a bearing insert distal surface which contacts the proximally facing surface of the baseplate part way towards a proximally facing surface of the bearing insert where it defines a slot bottom surface (a distally facing surface within the insert). A first leg of the U-shaped slot intersects the bore in the bearing insert. The bottom surface of the slot preferably lies in a plane containing a central axis of the insert bore. A second leg of the U-shaped slot includes a recessed groove for receiving a portion of the wire spring. The curved wire spring element may have a hairpin shape sized for insertion into the U-shaped slot. The pin may be cylindrical in crossection and extend along an axis and have a cross-bore extending generally perpendicular to the longitudinal direction of the pin. The cross-bore in the pin receives a free end of the wire spring element first leg such that when the first leg of the pin is deflected, the free end of the first leg can apply a biasing force tending to move the pin outwardly of the sidewall of the bearing insert. To accomplish this, the first leg of the slot includes an enlarged or widened portion extending in an anterior-posterior direction to accommodate the deflection of the first leg of the spring. The curved wire spring element has a U-shape or hair pin shape including the first leg, and has a second leg adapted to be located in a second leg of the complimentary U-shaped slot formed in the insert.

While the slot in the bearing insert has been described as U-shaped, it may be V-shaped with the apex of the V being rounded but with the legs of the spring not extending in parallel but at on acute angle to one another. Any design which can produce the requisite biasing of the pin outwardly of the side wall of the bearing insert and into engagement with a recess and a sidewall of the tibial base plate may be utilized without departing from the spirit and scope of the invention.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

DETAILED DESCRIPTION

Figure 1:
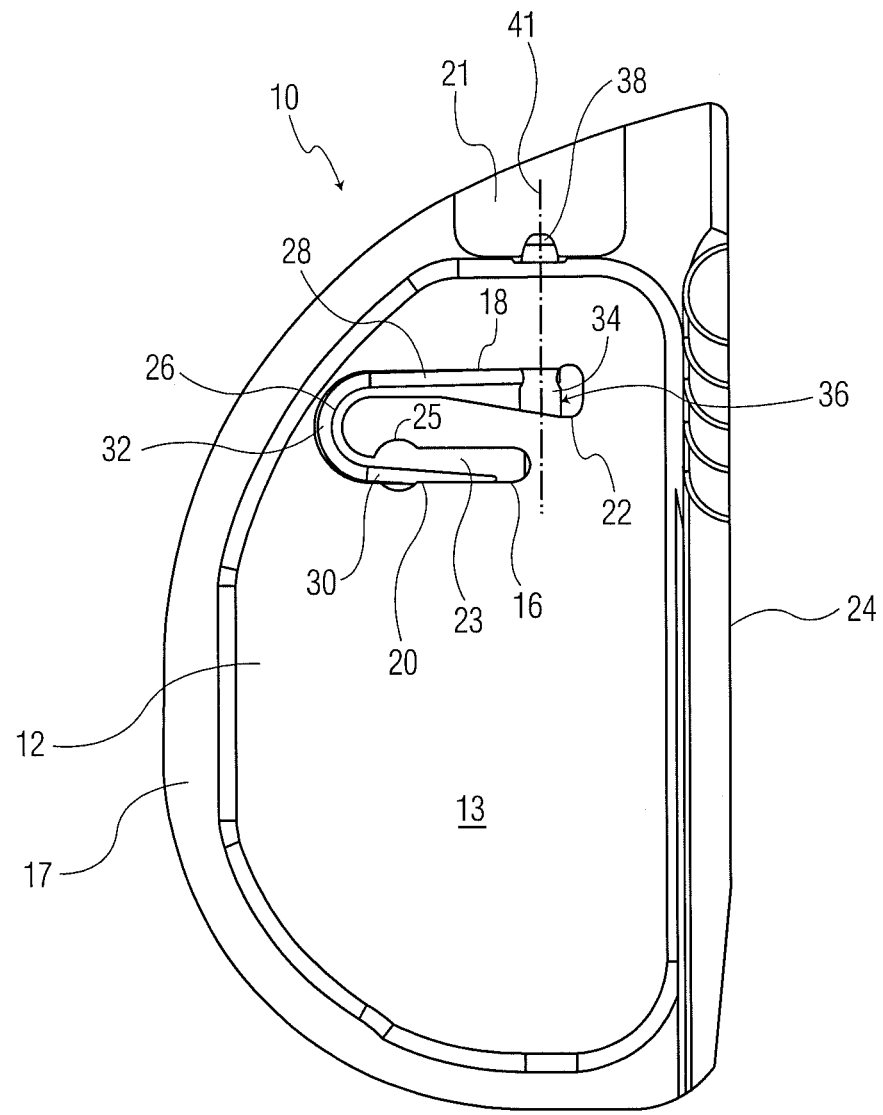
FIG. 1 is a bottom view of a tibial bearing insert with a locking pin of the present invention in an extended position.

Referring to FIG. 1, there is shown a bottom view of a tibial bearing insert generally devoted as 10. The insert is preferably made from ultra high molecular weight polyethylene (UHMWPE). The view of insert 10 as shown in FIG. 1 is a bottom view of a single condylar portion of a prosthetic tibial implant. While only one condylar portion is shown, the bearing insert 10 may be comprised of two (medial and lateral) bearing inserts which can be separate or can be joined together along an anterior bridge portion (not shown). The proximally facing surface of the tibial implant, best seen in FIG. 5, contains the prosthetic condylar bearing surface adapted to engage a corresponding condyle on the prosthetic femoral component (not shown). The insert 10 is preferably mounted on a metal tibial baseplate, or tibial tray in any conventional manner.

As can be seen in FIG. 1, a distal surface 12 is formed on a boss 13 extending from a distally facing shelf surface 17 which extends around a periphery of insert 10 at least on a lateral, anterior and posterior side. The distally facing surface 12 of bearing insert 10 is adapted to be mounted on the proximally facing surface of a tibial tray or base plate 14 as shown in cross-section in FIG. 5. Distally facing surface 12 includes a generally U-shaped recess 16 which is cut part way through the thickness of tibial bearing insert 10 but spaced sufficiently from the proximally facing condylar bearing surface 15 of tibial bearing insert 10 to not comprise the bearing surface. U-shaped recess or pocket 16 includes a first leg portion 18 and a second leg portion 20. Leg portion 20 may be shorter than leg portion 18 and is spaced a predetermined distance therefrom. First leg 18 has an end 22 located toward the medial edge 24 of insert 10. End 22 has a wider anterior-posterior dimension than the remainder of leg 18 of generally U-shaped recess 16. Recess 16 houses a bent spring element 26, which has a hairpin shape with first and second legs 28, 30 joined by a U-shaped portion 32. First leg 28 of spring element 26 engages a shaft 34 of a detent or locking pin 36. Pin 36 includes a tip 38. Tip 38 is preferably conically tapered toward its free end. Locking pin 36 may have a 0.070 diameter shaft 34 and may be 0.347 inches in length with tip 38 being rounded with a 0.025 radius. Spring element 26 may frame a 0.025 diameter with a longer leg being 0.335 inches long and a shorter leg being 0.220 inches long with a curved connecting portion having an inner radius of 0.70 inches and an outer radius of 0.095 inches. The legs may be angled away from one another about 10°. Spring element 26 may be placed in a recess having a width of about 0.045 inches expanding in with the end at a 10° angle for about 0.43 inches.

Figure 2:
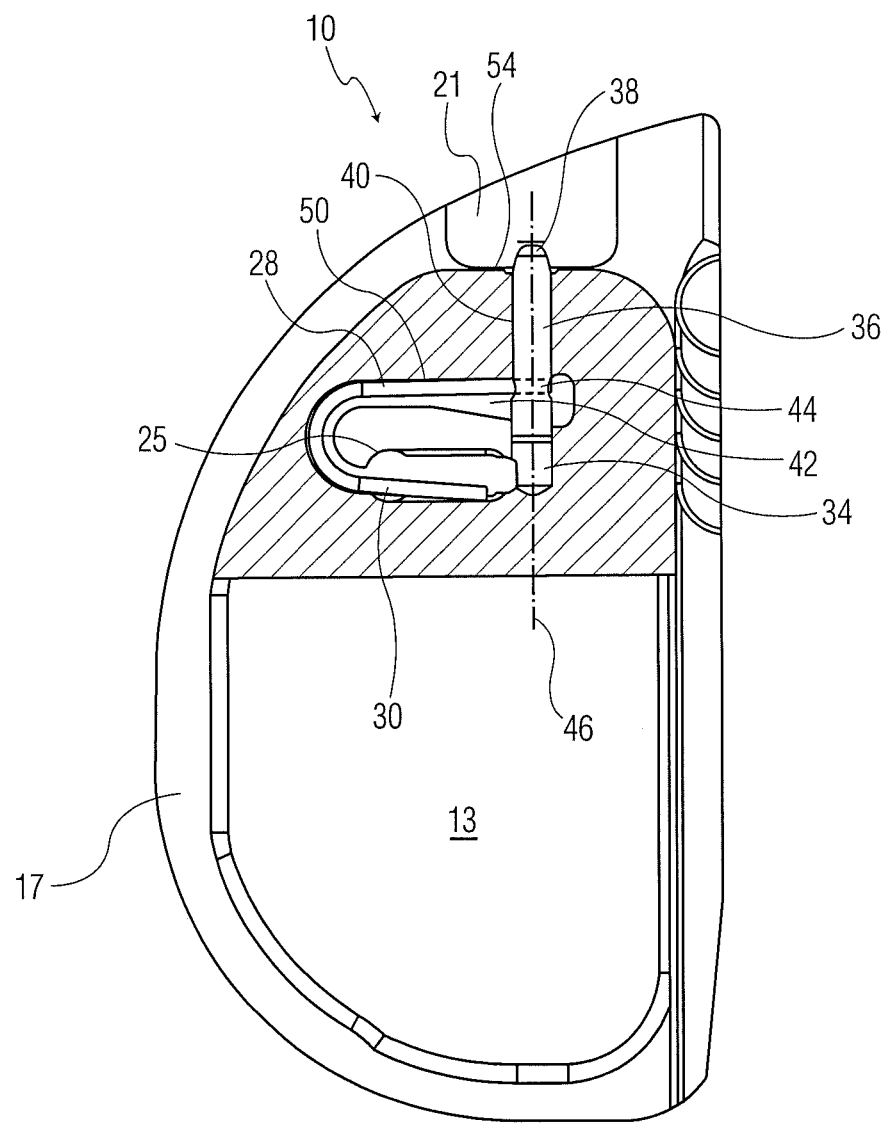
FIG. 2 is a bottom partial sectional view showing the locking pin of FIG. 1 in the extended position.
Figure 3:
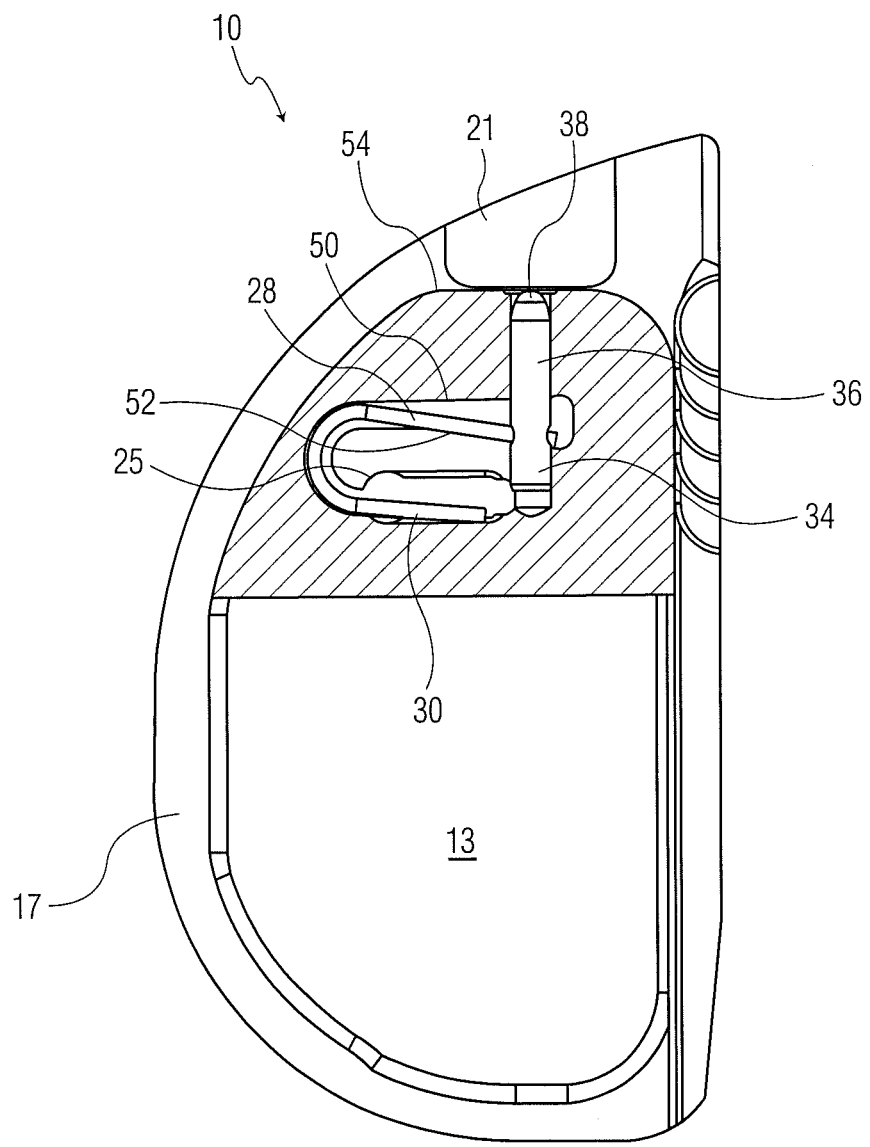
FIG. 3 is a bottom partial sectional view showing the locking pin in the compressed position.
Figure 7:
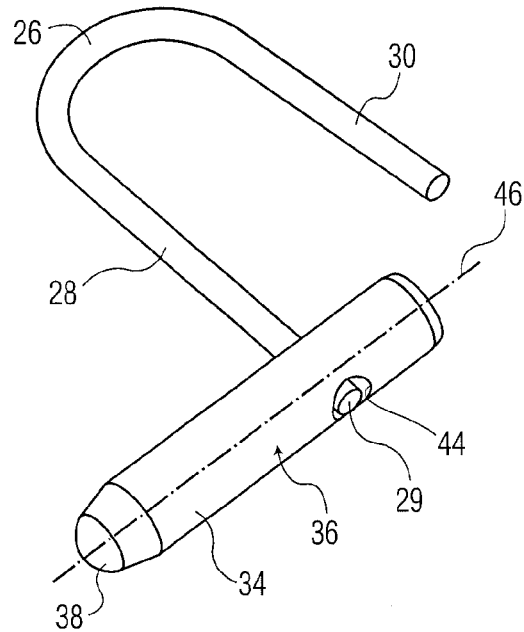
FIG. 7 is an isometric view of the locking pin and spring assembly of the present invention.

As best seen in FIGS. 2-3, which show a cross-sectional view through a portion of the tibial insert 10, pin 36 is mounted within a bore 40 formed in tibial insert 10. Bore 40 preferably has a central axis 46 lying in a plane 42, which may form the bottom surface of U-shaped recess or pocket 16. As shown in FIG. 7, free end 29 of first leg 28 of spring element 26 is inserted into a cross-bore 44 formed through pin 36. The axes of cross-bore 44 may be perpendicular to a longitudinal axis 46 of pin 36 when assembled axis 41 and axis 46 are coaxial.

Referring to FIG. 2, pin 36 is shown in a first extended position and, in FIG. 3, in a retracted position. As can be seen from FIG. 2 with pin 36 in the extended position, spring leg 28 is positioned against surface 50, which forms the anterior boundary of slot 16. Alternately, as shown in FIG. 3, leg 28 lies against surface 52, which is the posterior most surface of first leg 18 of the generally U-shaped slot when pin 36 is in the retracted position. When in the retracted position tip 38 of pin 36 is flush with a surface 54 of a wall 15 of boss 13 which is adjacent a pocket on recess 21 formed in insert 10.

Figure 4:
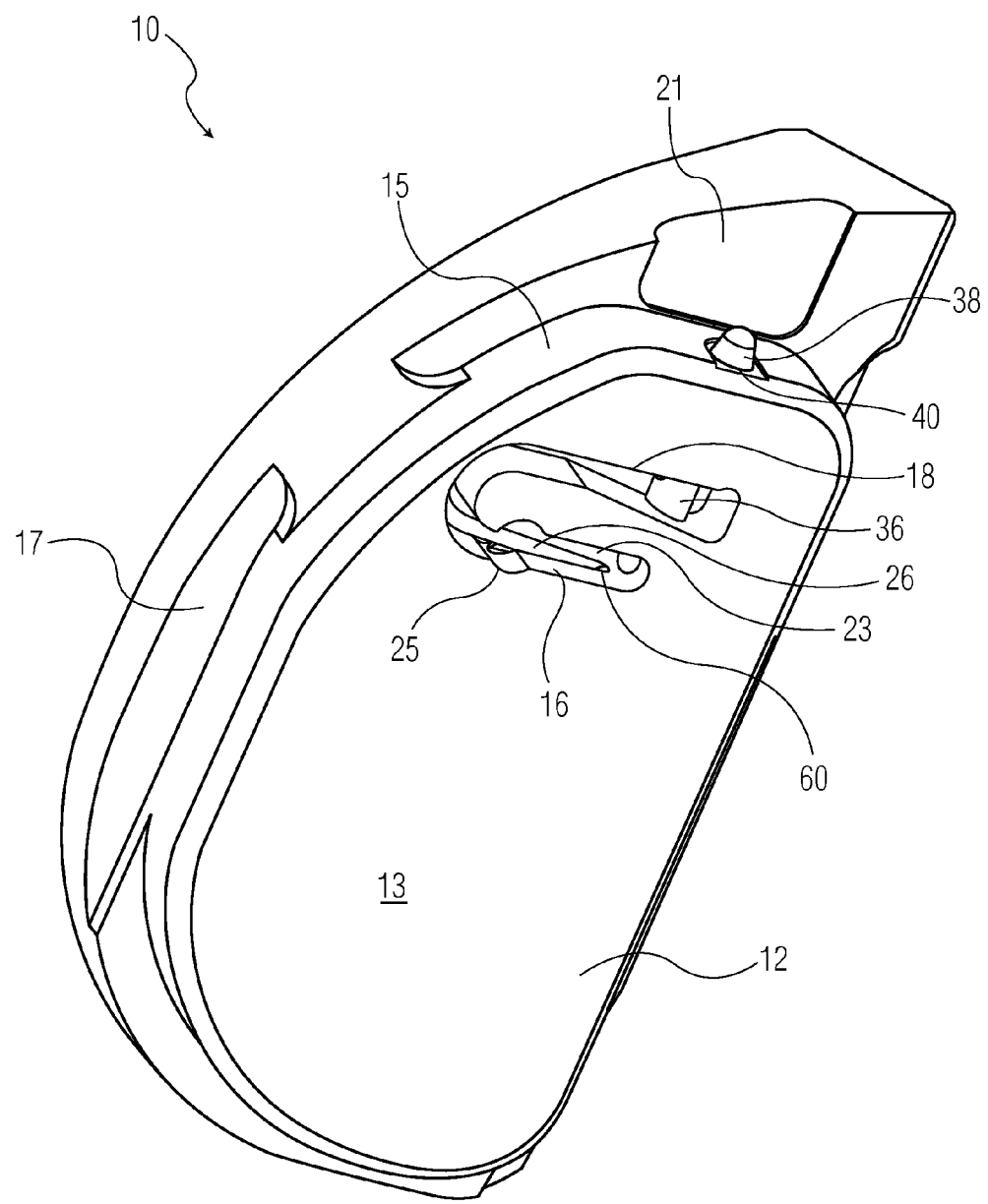
FIG. 4 is a bottom perspective view showing the locking pin in the extended position.

As best seen in FIG. 4, tibial insert 10 includes boss 13 defining a peripheral wall 15 which spaces distal surface 12 from distally locking surface 17 which upon assembly engages a proximally facing surface of a periphery extending sidewall of the tibial baseplate 14. A pocket or depression 21 is formed in surface 17 of insert 10 into which tip 38 of pin 36 extends when in the extended position shown in FIG. 2. Pocket or recess 21 receives an extension 55 formed on baseplate 14 which extension includes a bore 70 (shown in FIG. 5) for receiving pin 36 as will be discussed below.

The second leg 20 of U-shaped recess 16 may include an enlarged portion 23 including a circular portion 25 for providing access of the tool for forming a groove 60 at the bottom of recess 16. It can be seen that during assembly, pin 36 is first inserted into bore 40 in insert 10 and then first leg 28 of spring element 26 is inserted through crossbore 44 and then second leg 30 of spring element 26 is resiliently deflected toward first leg 28 and then inserted into the second leg 20 of recess 16.

Referring to FIG. 4, there is an isometric view of the insert of FIGS. 1-3 showing distally facing surface 13, sidewall 15, and shelf surface 17, including generally U-shaped recess or pocket 16 including spring 26. Second leg 20 of the generally U-shaped pocket 16 may include a groove 60 for receiving second leg 30 of spring 26. Groove 60 maintains leg 30 in place during shipping and handling to make sure that the spring element 26 is not dislodged from U-shaped pocket 16.

The general shape of the tibial insert 10 shown in FIG. 4 may be obtained by molding the bearing insert which is typically made of ultrahigh molecular weight polyethylene.

Figure 5:
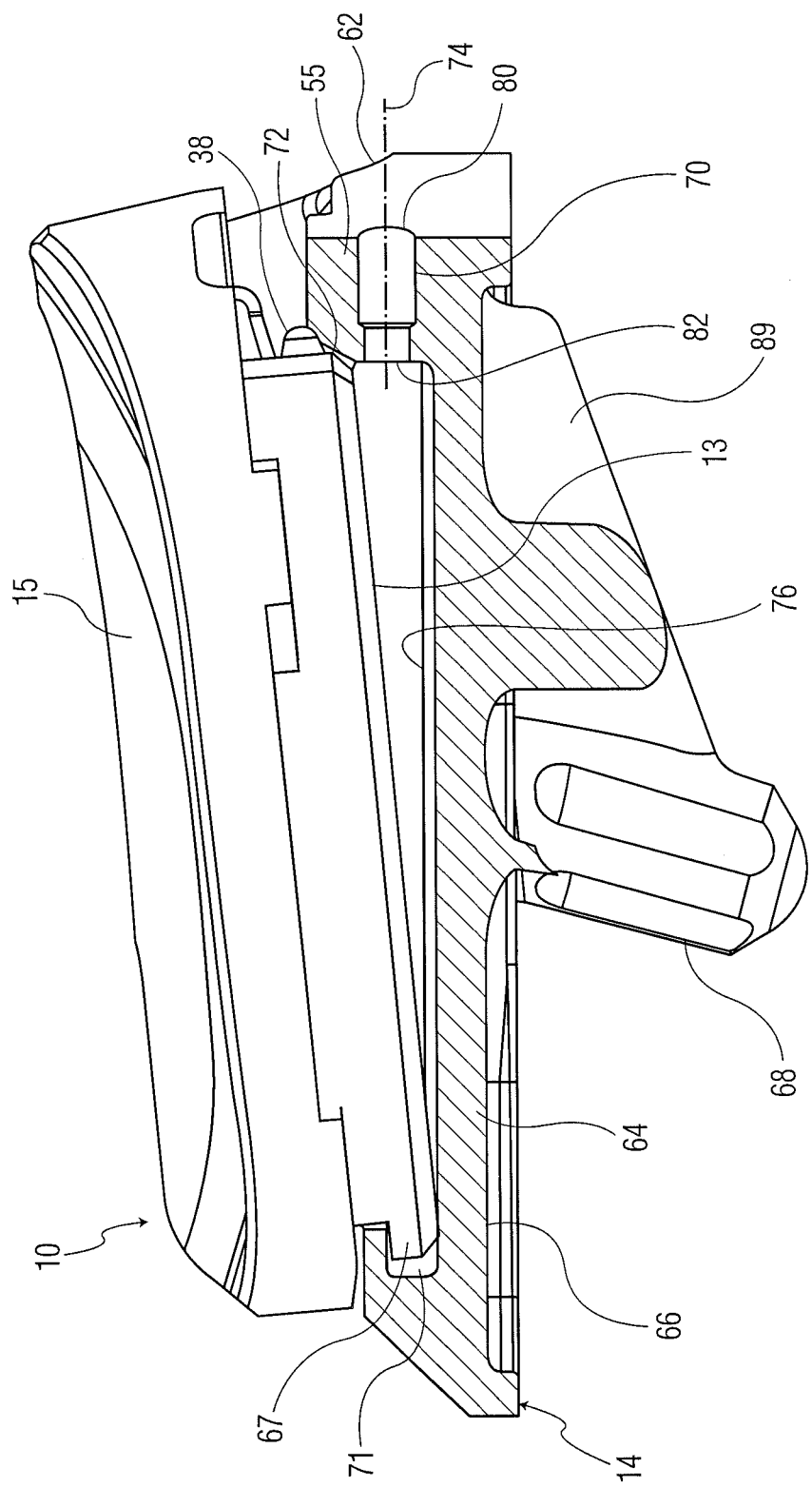
FIG. 5 is a lateral sectional view showing the bearing insert and tibial baseplate in the position for assembly with the pin in the extended position just prior to seating in the tibial baseplate.
Figure 6:
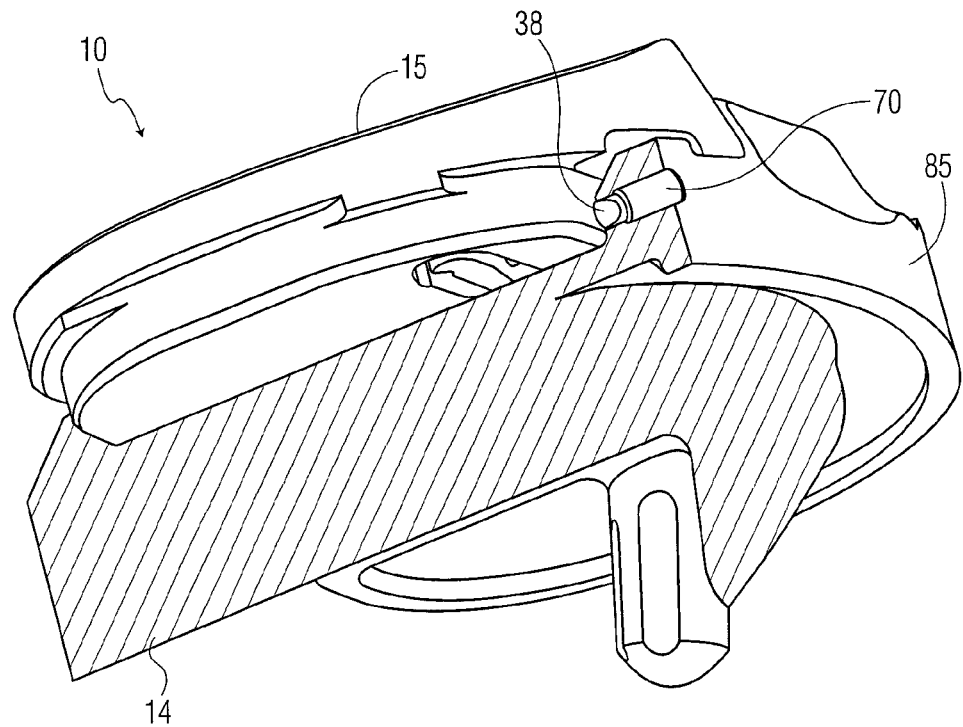
FIG. 6 is a sectional perspective view of the bearing insert and baseplate fully assembled with the pin in the extended position locking the bearing insert to the baseplate.

Referring to FIG. 5, there is shown tibial insert 10 being assembled to tibial baseplate 14. Tibial baseplate 14 is typically made of metal and includes a sidewall 62 surrounding a distal plate 64 which includes a distally facing surface 66 for contacting bone and a proximally facing surface 76. Baseplate 14 may include one or more peg-like extensions 68 for being inserted into the bone of a resected tibial plateau (not shown). As seen in FIG. 5, an anterior portion of sidewall 62 includes a bore 70 for receiving the tip 38 of pin 36. Sidewall 62 further includes an anterior ramp surface 72 adapted to engage conical tip 38 and force pin 36 inwardly against the force of spring 26 thereby compressing or deflecting the spring. Ramp portion 72 extends inwardly (i.e. posteriorly) on moving towards surface 76 of baseplate 14. As shown in FIG. 6, the axis 41 of bore 40 and axis 46 of pin 36 are aligned with an axis 74 of bore 70. At this point, tip 38 of pin 36 advances into the bore 70 thereby locking the baseplate 14 to the tibial insert 10. As can be seen in FIG. 5, tibial insert 10 includes a flange element 67 which slides into recessed area 71 of baseplate 14 so that with pin 36 engaged, the insert cannot move proximally out of contact with the baseplate. Thus, surface 13 of tibial insert 10 is in contact with proximally facing surface 76 of baseplate 14. While pin 36 and bore 70 are shown located in an anterior sidewall of baseplate 14, such could also be located on the lateral or anterior-lateral side thereof with a locking flange similar to flange 67 and recessed area such as 71 located on the anterior side. Of course any typical locking or snap connection design between the polyethylene bearing and the metal tray can be used with the locking pin of the present invention.

Referring to FIG. 6 there is shown an isometric view of tibial bearing 10 and tibial baseplate 14 partially cut away to show the bore 70 through the anterior surface 85 of baseplate 14. Tip 38 is shown partially within bore 70 thereby locking the polyethylene tibial bearing or trial bearing 10 to baseplate 14. Baseplate 14 may have a bone contacting surface including peg 68 and can have any typical bone interface design such as having a keel 89 best shown in FIG. 5.

Referring to FIG. 7, there is shown spring element 26 removed from generally U-shaped recess 16 showing spring 26 connected to pin 36 via cross-bore 44 in shaft 34. Also shown is the end surface 29 of leg 28, which extends flush with the outer surface of pin 36 when hairpin spring element 26 is mounted thereon.

As best seen in FIGS. 5 and 6, when the surgeon wishes to assemble the tibial bearing insert 10 into a baseplate 14, the surgeon inserts flange 67 into recessed area 71 and then pushes on the anterior surface of insert 10 distally causing tip 38 of pin 36 to engage ramp 72 which forces pin 36 posteriorly and further movement of insert 10 proximal to distal moves pin 36 in posteriorly on bore 40 against the force of spring 26 until aligned with hole 70 which allows pin 36 to snap into the bore 70. To remove the insert, the surgeon inserts a "pick," i.e., inserts an instrument having a diameter somewhat smaller than the diameter of bore 70 through an open end 80 of bore 70 and into engagement with tip 38 so that pin 36 may be pushed and moved inwardly against the force of spring 26 to the point where tip 38 is spaced inwardly of surface 82 on extension 55 of baseplate 14 which allows the surgeon to pivot bearing element 10 proximally about flange 67 and remove the bearing insert from the tibial baseplate. This can be accomplished without any damage to either the ultrahigh molecular weight polyethylene insert or the baseplate. The distance between surfaces 50 and 52 of the first leg 18 of recess 16 widens at end 22 so as to allow for sufficient deflection of leg 28 of spring 26 so that tip 38 of pin 36 can be moved flush with surface 15 of boss 13.

Figure 8:
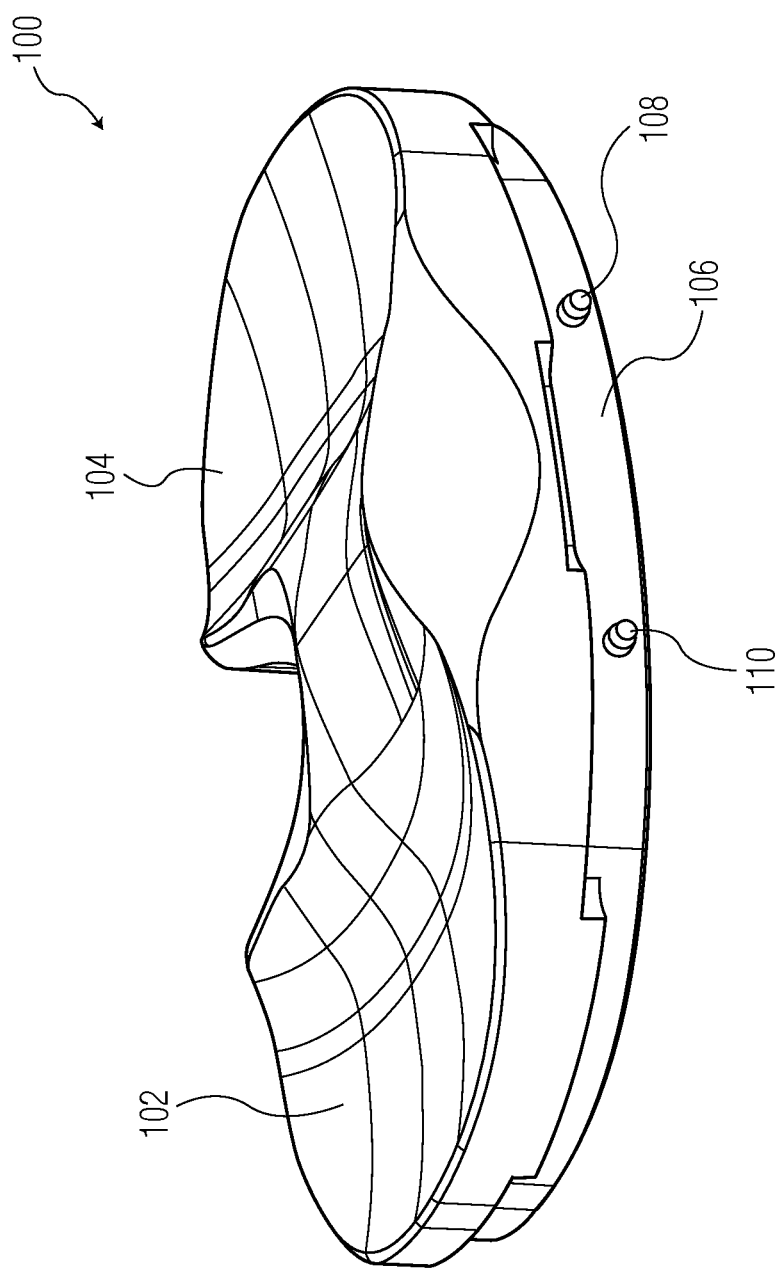
FIG. 8 is a tibial insert showing medial and lateral condylar portions with a pair of spring loaded pins extending from an anterior surface.
Figure 9:
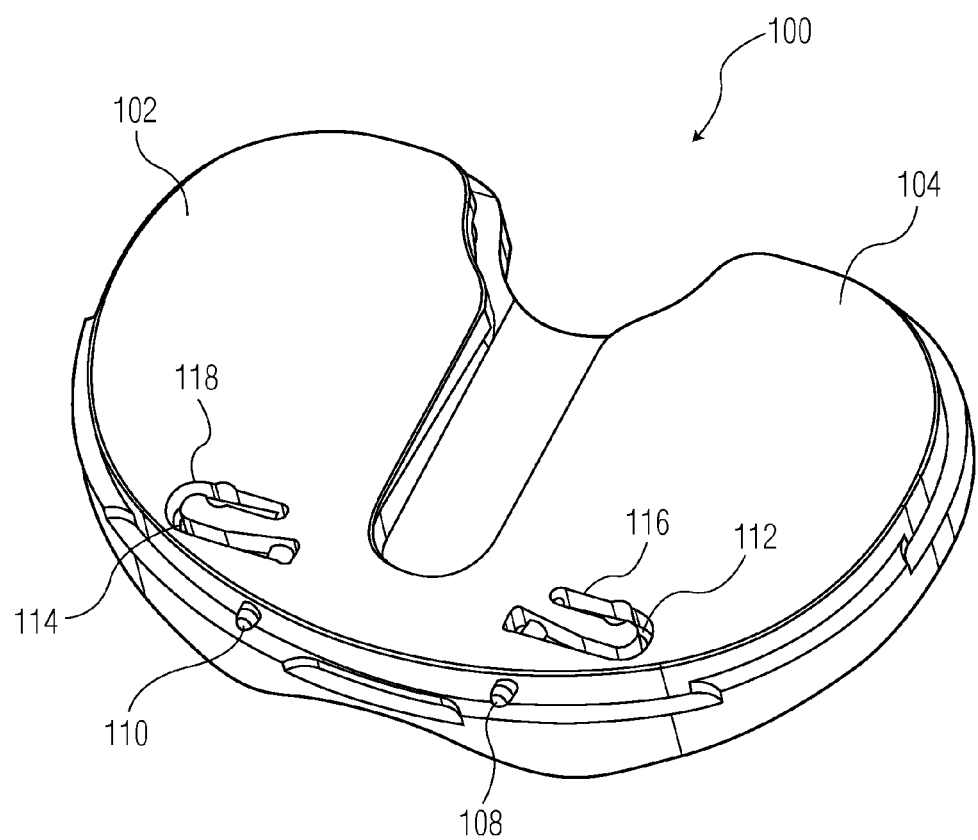
FIG. 9 is an isometric view of the distally facing surface of the implant of FIG. 8, including a pair of spring elements located in grooves formed on the medial and lateral sides of the tibial component.

Referring to FIGS. 8 and 9, there is shown a bi-condylar tibial implant bearing denoted as 100, including medial and lateral bearing surfaces 102 and 104, respectively. Implant 100 includes an anterior surface 106 and a pair of locking pins 108, 110. Bearing 100 is made of UHMWPE and is designed to be mounted in a metal tibial tray. The mechanism for locking the bearing in the tray is similar to that described above for a unicondylar implant.

Referring to FIG. 9, the implant 100 is shown viewing the distal surface 112 from an anterior direction, which surface 112 contacts a proximal surface of a standard tibial tray. Surface 112 includes locking elements 108 and 110. Locking elements or pins 108, 110 are biased by a pair of springs 112 and 114 set in a u or v-shaped groove 116 and 118, respectively. The design for a bi-condylar UHMWPE implant with the locking elements and grooves of FIGS. 8 and 9 in all respects identical to that described above for a unicompartmental polyethylene tibial bearing. As indicated above, the specific design of the bearing surface of the tibial implant is not material to the invention as long as the system for locking the polyethylene bearing on the metal tibial tray is similar with a posterior flanged portion for engaging a locking groove or recess in the metal tray and the anterior portion of implant 110 with the pair of pins 108, 110 for engaging a ramp on the metal tibial tray as described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A tibial implant comprising:
a baseplate having a distally facing bone contacting surface and a proximally facing surface surrounded at least in part by a proximally extending wall, the wall having a ramp surface extending from the wall towards the baseplate proximally facing surface and a receptacle located distally of the ramp;
a bearing insert mounted on the baseplate having a distally facing surface engaging the proximally facing surface of the baseplate, the bearing insert distally facing surface having a recess open to the bearing insert distally facing surface, the bearing insert having a side surface extending proximally away from the bearing insert distally facing surface and a passageway extending from the recess in the bearing insert distally facing surface to the bearing insert side surface; and
a spring detent having a pin mounted in the passageway of the insert and a curved wire spring element mounted in the bearing insert recess, the wire spring element having an end engaging the pin and biasing the pin outwardly of the bearing insert side surface, the pin having a tip portion extending outwardly from the bearing insert side surface, the tip engaging the ramp as the bearing insert is mounted on the baseplate proximally facing surface.
2. The tibial implant as set forth in claim 1 wherein the recess in the bearing insert is a u-shaped slot extending proximally from the bearing insert distally facing surface to a proximally facing surface of the bearing insert to define a slot bottom surface.

3. The tibial implant as set forth in claim 2 wherein a first leg of the u-shaped slot intersects the passageway in the bearing insert.

4. The tibial implant as set forth in claim 3 wherein the bottom surface of the slot lies in a plane containing a central axis of the insert passageway.

5. The tibial implant as set forth in claim 3 wherein a second leg of the u-shaped slot includes a recessed groove for receiving a portion of the curved wire spring element.

6. The tibial implant as set forth in claim 2 wherein the curved wire spring element has a hairpin shape sized for insertion into the u-shaped slot.

7. The tibial implant as set forth in claim 1 wherein the curved wire spring element has a free end and the pin has a bore receiving the free end of the spring.

8. The tibial implant as set forth in claim 1 wherein the curved wire spring element has a u-shape including first and second legs and the recess is formed as a complementary u-shaped slot.

9. The tibial implant as set forth in claim 8 wherein the first leg of the spring element has the end for engaging the pin, the first leg being longer than the second leg.

10. A tibial implant comprising:
a baseplate having a proximally facing surface surrounded by a peripheral side wall including an opening therein, the side wall having a ramp therein located proximally of the opening, the ramp extending further away from the side wall distally toward the base plate proximally facing surface;
a bearing insert mounted on the baseplate proximally facing surface and having a peripheral side surface adjacent the side wall of the baseplate, a recess in a surface of the bearing insert facing the baseplate proximally facing surface;
a pin mounted in the bearing insert having a first end extending into the bearing recess and a second end extending beyond the peripheral side surface of the bearing insert;
a spring element mounted in the bearing insert recess having a hairpin shape with a free end engaging the pin and biasing the pin outwardly of the bearing insert side surface, the pin having a tip portion extending outwardly from the bearing insert side surface, the tip engaging the ramp as the bearing insert is mounted on the baseplate proximally facing surface.

11. The tibial implant as set forth in claim 10 wherein the recess in the bearing insert is a u-shaped slot extending proximally from the bearing insert distally facing surface to a proximally facing surface of the bearing insert to define a slot bottom surface.

12. The tibial implant as set forth in claim 11 wherein a first leg of the u-shaped slot intersects a bore in the bearing insert.

13. The tibial implant as set forth in claim 12 wherein the bottom surface of the slot lies in a plane containing a central axis of the insert bore.

14. The tibial implant as set forth in claim 12 wherein a second leg of the u-shaped slot includes a recessed groove for receiving a portion of the spring element.

15. The tibial implant as set forth in claim 12 wherein the spring element has a hairpin shape sized for insertion into the u-shaped slot.

16. The tibial implant as set forth in claim 10 wherein the spring element has a free end and the pin has a bore receiving the free end of the spring.

17. The tibial implant as set forth in claim 10 wherein the spring element has a u-shape including first and second legs and the recess is formed as a complementary u-shaped slot.

18. The tibial implant as set forth in claim 17 wherein the first leg of the spring element has the end for engaging the pin, the first leg being longer than the second leg.

19. A tibial implant comprising:
a baseplate having a distally facing bone contacting surface and a proximally facing surface surrounded at least in part by a proximally extending wall, the wall having a ramp surface extending from the wall towards the baseplate proximally facing baseplate surface and a receptacle located distally of the ramp;
a bearing insert mounted on the baseplate having a distally facing surface engaging the proximally facing surface of the baseplate, the bearing insert distally facing surface having a recess open to the bearing insert distally facing surface, the insert having a side surface extending proximally away from the bearing insert distally facing surface and a passageway extending from the recess in the bearing insert distally facing surface to the insert side surface; and
a spring detent having a pin mounted in the passageway of the insert and a wire spring element mounted in the bearing insert recess, the wire spring element having an end engaging the pin and biasing the pin outwardly of the bearing insert side surface, the pin having a tip portion extending outwardly from the bearing insert side surface, the tip engaging the ramp as the bearing insert is mounted on the baseplate proximally facing surface.

20. A tibial implant comprising:
a baseplate having a distally facing bone contacting surface and a proximally facing surface surrounded at least in part by a proximally extending wall, the wall having a ramp surface extending from the wall towards the baseplate proximally facing surface and a receptacle located distally of the ramp;
a bearing insert mounted on the baseplate having a distally facing surface engaging the proximally facing surface of the baseplate, the bearing insert distally facing surface having a recess open to the bearing insert distally facing surface, the bearing insert having a side surface extending proximally away from the bearing insert distally facing surface and a passageway extending from the recess in the bearing insert distally facing surface to the bearing insert side surface;
a spring detent having a pin mounted in the passageway of the insert and a curved wire spring element mounted in the bearing insert recess, the wire spring element having an end engaging the pin and biasing the pin outwardly from the bearing insert side surface, the pin having a tip portion extending outwardly of the passageway in the bearing insert side surface; and
wherein the wire spring element has a free end and the pin has a bore receiving the free end of the spring.

21. A tibial implant comprising:
a baseplate having a proximally facing surface surrounded by a peripheral side wall including an opening therein, the side wall having a ramp therein located proximally of the opening, the ramp extending further away from the side wall distally toward the base plate proximally facing surface;
a bearing insert mounted on the baseplate proximally facing surface and having a peripheral side surface adjacent the side wall of the baseplate, a recess in a surface of the bearing insert facing the baseplate proximally facing surface;

a pin mounted in the bearing insert having a first end extending into the bearing recess and a second end extending beyond the peripheral side surface of the bearing insert;

a spring element mounted in the bearing insert recess having a hairpin shape with a free end engaging the pin and biasing the pin outwardly of the bearing insert side surface;

wherein the spring element has a u-shape including first and second legs and the recess is formed as a complementary u-shaped slot; and wherein the first leg of the spring element has the free end for engaging the pin, the first leg being longer than the second leg.

* * * * *